(12) United States Patent
Xing et al.

(10) Patent No.: US 8,778,654 B2
(45) Date of Patent: Jul. 15, 2014

(54) RECOMBINANT BACTERIA FOR PRODUCING DEOXYVIOLACEIN AND USES THEREOF

(75) Inventors: Xinhui Xing, Beijing (CN); Peixia Jiang, Beijing (CN)

(73) Assignee: Tsinghua University, Bejing (CN)

( * ) Notice: Subject to any disclaimer, the term of this patent is extended or adjusted under 35 U.S.C. 154(b) by 318 days.

(21) Appl. No.: 13/003,227

(22) PCT Filed: Apr. 22, 2009

(86) PCT No.: PCT/CN2009/000430
§ 371 (c)(1),
(2), (4) Date: Feb. 22, 2011

(87) PCT Pub. No.: WO2010/003304
PCT Pub. Date: Jan. 14, 2010

(65) Prior Publication Data
US 2011/0183384 A1    Jul. 28, 2011

(30) Foreign Application Priority Data

Jul. 11, 2008 (CN) .......................... 2008 1 0116601
Oct. 17, 2008 (CN) .......................... 2008 1 0224359

(51) Int. Cl.
| | | |
|---|---|---|
| C07H 21/00 | (2006.01) | |
| C12N 1/21 | (2006.01) | |
| C12N 15/00 | (2006.01) | |
| C12P 17/10 | (2006.01) | |
| C12P 21/00 | (2006.01) | |

(52) U.S. Cl.
USPC .............. 435/252.3; 435/252.33; 435/252.34; 435/320.1; 435/69.1; 435/121; 536/23.2

(58) Field of Classification Search
USPC ........ 435/252.3, 252.33, 252.34, 320.1, 69.1, 435/119; 536/23.2
See application file for complete search history.

(56) References Cited

FOREIGN PATENT DOCUMENTS

| CN | 101139654 A | 3/2008 |
|---|---|---|
| CN | 101319219 A | 12/2008 |
| CN | 101368169 A | 2/2009 |
| WO | WO 02/50299 A2 | 6/2002 |
| WO | WO 2010/003304 A1 | 1/2010 |

OTHER PUBLICATIONS

Brady et al., Organic Letters 3(13):1981-1984, 2001.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Lee et al., Applied and Environmental Microbiology 61(6):2211-2217, 1995.*
Sanchez et al., ChemBioChem 7:1231-1240, 2006.*
Kleber-Janke et al., Protein Expression and Purification 19:419-424, 2000.*
Brady et al., GenBank accession No. AF367409, 2002.*
Vasconcelos et al., GenBank accession No. AE016825, 2005.*
Sousa et al., Microbiology 148(Pt5):1291-1303, 2002.*
Ausubel, F., Current Protocols in Molecular Biology, Hybridization Analysis of DNA Blots, pp. 2.10.8-2.10.11.*
International Search Report for Int'l Application No. PCT/CN2009/000430; Date Mailed: Jul. 16, 2009.
Haisheng, W. et al., "Recent Research Progress of Bacterial Violaccin," Chemical Industry and Engineering Progress, ISSN 1000-6613, vol. 27, No. 3, Mar. 31, 2008, p. 315-321, see the whole document.
Brady, S.F. et al., "Cloning and Heterologous Expression of a Natural Product Biosynthetic Gene Cluster from cDNA," Org. Lett., vol. 3, No. 13, Jun. 28, 2001, p. 1981-1984, see the whole document.

* cited by examiner

*Primary Examiner* — Delia Ramirez
(74) *Attorney, Agent, or Firm* — Alleman Hall McCoy Russell & Tuttle LLP (57) ABSTRACT

Recombinant bacteria for producing deoxyviolacein and uses thereof are provided, wherein the recombinant bacteria is obtained by introducing the deoxyviolacein synthesis-related gene cluster into *Escherichia coli* BL21-CodonPlus (DE3)-RIL or *Pseudomonas putida* mt-2. The deoxyviolacein synthesis-related gene cluster is obtained by knocking out VioD gene from the violacein synthesis-related gene cluster composed of VioA, VioB, VioC, VioD and VioE, and the nucleotide sequence is as shown in the SEQ ID NO: 1 in the sequence listing. A method for producing deoxyviolacein by fermenting the recombinant bacteria to produce deoxyviolacein by using L-tryptophan as substrate is provided. The method has high efficiency of deoxyviolacein production, the deoxyviolacein produced is convenient to be extracted, and simple to be separated and purified.

7 Claims, 3 Drawing Sheets

SEQUENCE LISTING

```
<160> NUMBER OF SEQ ID NOS: 1

<210> SEQ ID NO 1
<211> LENGTH: 6197
<212> TYPE: DNA
<213> ORGANISM: Duganella sp.B2 CGMCC 2056

<400> SEQUENCE: 1
atgacaaatt attctgacat ttgcatagtt ggcgcaggca taggggcct  cagttgtgcg      60 acccagttga tcaacgccgc cgccggcaag aatttacgga tcagggtgtt cgacatggat     120
acgacggtgg gcgggcgcat ccagtcgcat aaagtagacg aggaggaaat cgccgaactc     180
ggcgccgccc gctactcgcc gcaactccat ccgcatttcg agcaactcat gcaggaatgc     240
gggctggcgc atgcgaccta ccctttcacc caggtggtgt cgctcgatca ggcgcaggag     300
aaactgaagg caactctgct gagcctgagt gcgatgctga aaaaacatcc gaacgattcc     360
ttccttgaat tcgtcagcca gtacctgggc gccgccgaag cgacccgcat gatcaaggcg     420
accggttacg acgccttgct gctgccggtg gtctcggcag cgatggccta cgacatcatc     480
aaaaagcacc cggaaacaca aagctttacc gaaaacgccg ccaacgagtg gcgctatgcc     540
accgacggct acagcgagct gctgcgtcag ttgcagcgcc aggcccagga cgccggcgtg     600
gaattccggc tggggcatcg cttgctgtcg gttgaaaagt ccggcaccga ccatgtcctc     660
gccttccgcc atatgggcga tactcagatg caccgggcgc gccatgtgat cacgaccctc     720
ccgccgaccg ccatgaagcg cctgaacatg gattttccgg ccgccttcag tcccttccag     780
tacgattccc tgcctttgtt caaaggattc ctgaccttcg aaacagcctg gtgggacgcg     840
ctcgggctga ccgacaaagt gctgatggcc gataatcctc ttcggaaaat ctacttcaag     900
```

```
ggcgacaaat acctggtgtt ctacaccgac agcgccagcg ccacctattg gcgggagtac    960
ctggagcaag gggaagacgt ttacctggac cgggtccgcc atcacctgaa agaagtgctg   1020
ccgctgaacg tcagccgct gccgcagatc aaggcgcatt tttacaagca ctggccgcat   1080
ggcgtcgagt tcagcctgga gccggaagcc gagcatccag caaccctgct ccaccgcgac   1140
ggcatcatct cctgctcgga cgcgtatacc tcgcattgcg gctggatgga aggcagcttg   1200
atcagcgccg ggcacgctac ccgcctgttg ctggaacggc tcagccatcc gccagcacaa   1260
tccgggcacg actttaccct cgccacctct cttactgagc gcgcatgagc attctcgact   1320
ttccccgctt tcatttttcgg gggttttgccc gcgctaatgt gcccactgcc aaccgcaata   1380
cgcacggcca tatcgatatc gcgacgaatg cggtatcgat cgcgggcgaa ccattcgacc   1440
tgagccgccc gccgtcggaa ttccatgagc acatgaaaca gcttgctccc aggttcgatg   1500
cggcgggcaa gccggatccg gagggcatct tcagcgaggc ggccggctac aattttttgcg   1560
gcaacaatca cttttcgtgg gaaaacgcca ggatcaccgg cgtccagctg cgcgatggcg   1620
aggtcgatac cgaggacgcg ctggtcggcg ccaagctggc cctgtgggga cattacaacg   1680
actatctgcg caccacggtc aaccgcgcca gatgggtcga caacaacccc gccgagccgg   1740
acaccaccct catttacgcg ggccagttca cgctcagcgg caagcaagcc acgcccaaca   1800
caccgagcct gttcagcgcc gatatcgggc aggcgcattc ggtacgctgg gtcggcagcg   1860
gccatatcag cgagcgcagc gggcatttt tcgacgatga attcggccgt tccaggctgt   1920
tccagttttc cgtggcgaag ctcgatccgc atttcctctt caatccggac acaccgctgc   1980
cggccagcat gcgcgccttg caagaggcgc ttgccgacga ggatgtgctg gggctgacgg   2040
tccagtatgc gctgttcaat atgtcgacgc cgcagaaacc cgattcgccg gtgttctacg   2100
acctggccgg cggcatcggc ctgtggcgcc gcgacgagct ggccaccat ccggccggcc   2160
gtttgctgct gccgcgccag agcagcctgg ggcggtact ggtgaaggtg catgcggacc   2220
gggtgtcggt gaatatgccg acggccatcc cgttcaccac gcgcgaggcc ggcgccgtgt   2280
ccgaacagca tcctacccat gcgctgggcg gcaagcttgc gctgggcgat ctcatgctgc   2340
acggtgccac cggcaagctg atcgcccgca tcccgcaaca gctgtacctc gactactggc   2400
gccatcatgg tgtcttcgat gtgccgctgc tccacccggc cacggcctcg ggttcgctca   2460
gcatgtccag cgcgcaggcg cagtgggacg aagccgactg ggtgctgcag tccgacagca   2520
accatctgta tctggaagcg cccaaccggc aacgacagca ggactttccg cagacgatca   2580
cggtacaaag ccgcttgcgc ggcgagctgg cggcgcatcc ggcgctgacg gcgcaggcgc   2640
aggatggcga gatcgtcggc gtgcgcgtgg cgccatcggc gctgggagtt ggctatgcgg   2700
acctgacccct cacgggccgc cgttcaggcg cgacccgcat catgctgggc gaggcacagg   2760
ggcagcagtt catcggcgcg agggtgctgc ccgacgactg gcatctggac gacataccgg   2820
ccgaacaggt cgattacgcc tttctctacc agcacgtgat gagctactac gagctggtct   2880
atcccttcat gtcggacaag gtgttcagcc tggcggacca ctgcaagtgc gaaacctatt   2940
cgcgcctgat gtggcagatg tgcgatccgc agaaccggga caagagctat tacatgccga   3000
gcacgcgtga actgtcgctg ccgaaatcgc gcctgttcct gaaatacctg acccaggtcg   3060
aagcggccgc caagtccacg cttcctcaag cggtcgcacc gcatgtcatc ggctgcaagg   3120
ccgagtggat cgccgagctg aaaaaggcga tcgacctgga actgtcgctc atgctgcagt   3180
acctgtacgc cgcgtatgcc attcccaact atgcgcaggg agtgaaactg gtcgaggccg   3240
```

```
gccgctggct gccggacgag ctggagctgg cctgcggcac cgaggaccgg cgccgcaaca    3300
gcggagcgcg tggcgccctg ctcgaaatcg cccatgaaga aatgattcac tacctgatgg    3360
tcaacaatgt gctgatggcg ctcggcgagc cgttctacgc cggcgccccg cgctgggag     3420
aacaggcgcg ccagcgcttc ggcctggaca cggaatttgc cttcgaccct ttttccgagc    3480
atgtgctggc cagattcgtg cgtttcgagt ggcccgacta tcttcccacg cccggtaaat    3540
cgatcgccac cttctatgcg gcgatccgcc aggccgtggc cgatctgccc gatctgttcg    3600
acgccgacgg cggcaaacgc ggcggcgagc accacctgtt cctcaaagag ctcaccaacc    3660
gcgcctatcc cgcctatcag ctggaagtta gcgaccgcga cagcgcgctg ttcgcgctcg    3720
acttcgtcac cgaacagggc gaaggggtgg cggtggaatc gccccatttc gccgtgtcgc    3780
atttccagcg gctgcgcgcc ctggccggcc gcttttcggc acgcgaaaaa ccgttcgaac    3840
cggccgtgcc ggcgctgaaa aatccggtac tcgacccacg cgccgactgc accgtggtga    3900
ccgatcccaa ggcccgttcg ctgatgcagc tctaccaggg ctgctatgaa ctgaccttcg    3960
cgctgatggc gcaccacttc gcgcaaaagc cgctgggcag cctgcgccgc tcgcgcctga    4020
tgaatgcctc catcgacatc atgaccggtt tgctgcggcc cttgtcggcc gcgctgatga    4080
acatgccgtc cggcgtaccc gggcgcaacg ccggaccgcc cgtgcccggg ccggccgaca    4140
ccgccatcag cagtgactac agcctgggat gcgagctgct ggcgcagaaa tgcctggccc    4200
tggcgcagta cgcgcgcagc ctggaggccg aggtggccag cacggcgcag atcgacatgt    4260
tggagttctt taatcagcaa ctgaccgatt tatctcgggg aaagatgtca agagaggcct    4320
gaatgcacaa aatcatcatc gtgggcggcg gcctggcggg cagcctgacc gccacttatc    4380
tggcgcagcg cggacatgag gtccacgtta tcgaaaagcg cggcgatccg ctgcgggcgg    4440
agtcagccaa cgccgatccg gtcaactcgc gcgccattgg cgtgagcatg accgtgcgcg    4500
gcatcaaggc agtgctggcg gccggcatca gcaaggagga gctcgatcgg tgcggcgaac    4560
cggtcgtcgg catggcattt tcggtcgcg gcggccacaa ggtgcgcgaa ctgaccccgc    4620
tcgaaggctt gtttcccttg tcgctggacc gcaccgcgtt ccagcgcctg ctgaacaagt    4680
acgccgtcat gcacaaagtg aactattact tcgagcataa atgcctggac ctggacctgg    4740
acaagaaatc cgtgctgatc cagggcccgg acggcgcctt gcggcatctg caaggcgacc    4800
tgatcatcgg ggccgacggc gcccactccg ccgtgcggcg cgccatgcaa gccggcatgc    4860
ggcgcttcca gttcgaacaa tccttcttcc gccacggcta caagaccctg gtactgccga    4920
acgccgcggg actgggcttc cgcaaggatc tgctgtattt cttcggcatg gattccaagg    4980
gccagtttgc cggccgcgca gccaccatcc cggacggcag catcagcttc gccctctgcc    5040
tgccctacac cggcacgccc agcctggcca cgcgcgaccg cgccgccatg ggggagtttt    5100
tcagccgcta cttcggcatc ctgccaccgg ccagccggga agagctggtg aatcagttca    5160
tcgcgctgcc tagcaacgac ctcatcaatg tccgctccag caccttccat tacaagagca    5220
atgtcctgct gatcggcgat gcggcgcatg cgaccgcccc cttcctcggt cagggcatga    5280
acatggcgct ggaagacgtc tacgtcttca tcaccttgct ggaaaagcat cgcgatgacc    5340
tgggcctggt cttgtcggag tttacggggc agcgcaaggt gcaggccgac gccatgcagg    5400
atatggcgat cgccaactac gaaatgctga gcaacccgaa ttttatttc ttcctgcaaa    5460
cccgctacac ccgctacatg cacaagaaat ttcccagtgt ttatccgccc gacatggcgg    5520
agaagctgta cttcacatcg gttccctacg atgtgctgca acaaatccag aagaagcaaa    5580
acgtttggta caaacttgga agggtaaact aaggagacgc catgccaccg cacgccaccc    5640
```

```
cgccgctgct gccgatgcaa tggagcagcg cctacatctc gtattggtcg ccgatgcggg      5700
aagacgacga ggtcacttcc ggctattgct ggttcgacta tgcccgcgac atttgccgca      5760
tcgacggcct gttcaatccc tggtcggaaa aggagacggg acaccggctc tggatgtcgg      5820
aaatcggcga cgccaggcgc ggacaaagcc gcaaacagaa agtcgcttat gccagggagg      5880
cggagccggc cggcgtgaag ctgtacgagc gggcgctggc cgatgaggtc acgcccttcc      5940
acgagctgtt cctgccgcag gcgatcctga tcgacggcga agcgcgtcat gacgccgcc       6000 acacggtgct gggccaggcg gccgacgcct gggtggtgga gcggccgggc aaagccgcct      6060
cggtgttcta tctccaggcc ggcggcaatc acttgctgcg catggtcacc ggcaacgacg      6120
cgcagcatca gtcggtacgc gactttccga acttccttgc cggcgacatc gcggccagcg      6180
ttttcgtgtc ggaataa                                                     6197
```

RECOMBINANT BACTERIA FOR PRODUCING DEOXYVIOLACEIN AND USES THEREOF

This application is the U.S. National Stage of International Application No. PCT/CN2009/000430, filed Apr. 22, 2009, which designates the U.S., published in Chinese, and claims priority under 35 U.S.C. §§119or 365(c) to Chinese Application No. 200810116601.3, filed Jul. 11, 2008 and Chinese Application No. 200810224359.1, filed Oct. 17, 2008.

FIELD OF THE INVENTION

The invention relates to recombinant bacteria for producing deoxyviolacein and uses thereof.

BACKGROUND OF THE INVENTION

Violacein is a secondary metabolite produced by microbes. It is a blue-violet pigment and insoluble in water. Violacein is an indole derivative formed by the condensation of two modified L-tryptophan molecules. Since violacein was found in late 19th century, studies have been done to explore its biofunction. Recently, intensive research has found that violacein displays important biological activities as a potential anti-tumor, antiviral drug and bio-dye. Violacein has received much attention due to its broad application prospects in textiles and dyeing, plant pathogenic fungi control and medicine field such as viral and tumor therapy.

Studies have indicated that violacein has the following bioactivities: (1) Broad-spectrum antibacterial activity such as *staploylococcous aureus, Bacillus* sp, *streptococcus* sp, *mycobacterium, Neisserig, pseudomonas* (Sanchez et al., Reevaluation of the Violacein Biosynthetic Pathway and its Relationship to Indolocarbazole Biosynthesis. Journal 2006. 7, 1231-1240); (2) antioxidant activities (Konzen et al., Antioxidant properties of violacein: possible relation on its biological function. Journal 2006. 14, 8307-8313); (3) anti-tumor activities (de Carvalho et al., Cytotoxic activity of violacein in human colon cancer cells. Journal 2006.); (4) anti-viral activities; (5) anti-protozoan; and (6) process various texture as natural bio-dye (Akira SHIRATA, Isolation of Bacteria Producing Bluish-Purple Pigment and Use for Dyeing. Japan Agricultural Research Quarterly. 2000. 34). In a word, violacein possesses significant medical values and broad prospect of industrial application.

Among the violacein-producing strains, most research has been focused on the strain *Chromobacterium violaceum*. The complete genome sequence of *C. violaceum* was completed in 2003, and this provided the basis for the violacein biosynthesis pathway analysis and application. However, the violacein biosynthetic gene cluster was originally reported to be consisted of four related genes. Recently, the whole violacein biosynthesis pathway was almost clear till the fifth gene (vioE) was found. The violacein biosyntheis involves one cluster consisting of five genes including vioA, vioB, vioC, vioD, and vioE respectively and span 7.3 kb.

Deoxyviolacein is a structural analog of violacein with one less oxygen atom and generally appears as a by-product in violacein biosynthesis. Due to the very low proportion of deoxyviolacein in the blue-purple pigment with the amount of only one tenth of violacein production, it is difficult to get enough deoxyviolacein for the analysis of its properties and function. To date, few research works have been done internationally on methods and technologies of the deoxyviolacein isolation. Moreover, little research work has been done on the properties and bioactivities of deoxyviolacein due to its low production and the difficulties on the isolation and purification. Currently, no specific function could be assigned to deoxyviolacein except its inhibitory activity on protozoa (Matz, C et al. Marine Biofilm Bacteria Evade Eukaryotic Predation by Targeted Chemical Defense. PLoS ONE, (2008) 3(7): e2744). Our previous research indicated that deoxyviolacein had better dyeing effect and anti-bacterial activity than violacein. Thus, it is possible to speculate that deoxyviolacein can have potential applications as violacein, and strengthening the basic and applied research on deoxyviolacein has important scientific and application value. Currently, it is urgent to invent effective ways for efficient production of deoxyviolacein.

INVENTION DISCLOSURE

The objectives of the presented invention are to provide a recombinant bacterium for effectively producing deoxyviolacein and uses thereof.

The recombinant bacterium for producing deoxyviolacein is obtained by introducing a deoxyviolacein synthesis-related gene cluster into *Escherichia coli* BL21-CodonPlus (DE3)-RIL or *Pseudomonas putida*. The recombinant bacteria could produce deoxyviolacein by fermentation using L-tryptophan as the substrate.

Where, the deoxyviolacein synthesis-related gene cluster is obtained by knocking out VioD gene from the violacein synthesis-related gene cluster composed of VioA, VioB, VioC, VioD and VioE.

Wherein, the gene cluster described before includes the genes shown in the following 1) or 2) or 3).

1) The nucleotide sequence is shown in the SEQ ID NO: 1 in the sequence listing.

Under strict conditions, the DNA molecular could hybridize with the nucleotide sequence as shown in the SEQ ID NO: 1 in the sequence listing, and codes four enzymes VioA, VioB, VioC, and VioE in the biosynthesis pathway of violacein.

2) the DNA molecular exhibits over 99% nucleotide sequence identity with genes in 1), and codes four enzymes VioA, VioB, VioC, and VioE in the biosynthesis pathway of violacein.
3) the DNA molecular in step 3) has preferably at least 75% nucleotide sequence identity with genes in 1).

The exacting condition is that in a solution with 6×SSC and 0.5% SDS, hybridize at 68° C., and then wash the membrane once in 2×SSC/0.1% SDS and 1×SSC/0.1% SDS, respectively.

The deoxyviolacein biosynthesis gene cluster also lies within the protection scope of this invention.

The recombinant bacterium obtained by introducing the gene cluster into *Escherichia coli* BL21-CodonPlus (DE3)-RIL was named as *E. coli* BL-DV.

*E. coli* BL-DV had been deposited in China General Microbiological Culture Collection Center (CGMCC, their address is: Da Tun Road, Chao Yang District, Beijing, Institute of Microbiology Chinese Academy of Science, post code: 100101) on Jun. 25, 2008, and the accession number of the deposit is CGMCC No. 2557.

The recombinant bacterium obtained by introducing the gene cluster into *Pseudomonas putida* mt-2 NCIMB 10432 was named as *P. putida*-VioΔD, which has been deposited in China General Microbiological Culture Collection Center (located at No. 1 West Beichen Road, Chaovang District, Beijing 100101, China) on May 28, 2014, and the accession number of the deposit is CGMCC No. 9255.

The recombinant expression vector containing expression cassette with the gene cluster or the gene cluster or the expression cassette also lies within the protection scope of this invention.

The Second Objective of the Present Invention is to Provide a Method for Producing Deoxyviolacein.

The method for producing deoxyviolacein is provided by fermenting the recombinant *E. coli* or *P. putida* using L-tryptophan as substrate.

Taking the *E. coli* BL-DV as an example, when using the *E. coli* BL-DV to produce deoxyviolacein, the concentration the of L-tryptophan is 0.3-0.5 g/L fermentation medium, specifically, 0.4 g/L. The fermentation temperature is 10-37° C., specifically 20° C. The inducer was added into the recombinant bacterium when the cell concentration reaches to $OD_{600}$=0.6-1.0, which is also included in the method. Preferential, inducer was added when the cell concentration reaches $OD_{600}$=0.8, the inducer is selected randomly. IPTG is used as the inducer of the *E. coli* BL-DV CGMCC No. 2557, the concentration of IPTG is 0.7-1.3 mmol/L, specifically 1.0 mmol/L.

Taking the recombinant *P. putida*-VioΔD as an example, when using the *P. putida*-VioΔD to produce deoxyviolacein, the concentration the of L-trptophan is 0.3-0.5 g/L fermentation medium, specifically 0.4 g/L. The fermentation medium is any culture medium for *P. putida* growth, specifically: NaH2PO4.2H2O 1.0-2.0 g/L, Na2HPO4.12H2O 3.0-4.0 g/L, NH4Cl 0.5-1.0 g/L, K2HPO4.3H2O 7.0-8.0 g/L, 100 mM MgSO4.7H2O 10-15 mL/L, glycerol 3-4 mL/L and yeast extract 0.5-1.5 g/L, and the solvent is water. Inducer was added into the recombinant bacterium when the cell concentration reaches $OD_{600}$=1.0, which is also included in the method, the inducer is selected randomly. n-alkane with carbon number greater than 6 is used as the inducer for *P. putida*-VioΔD, specifically n-octane, and the concentration of n-octane is specifically 0.05 ml/100 ml medium. The fermentation temperature is set at 20° C.

THE BEST MODE OF CARRYING OUT THE INVENTION

The below experimental methods of the implementation, unless otherwise stated, are routine methods.

Embodiment 1, the recombinant strain for producing deoxyviolacein

1) Deoxyviolacein biosynthesis related gene cluster

*Duganella sp.*B2 CGMCC No 2056 was inoculated into liquid medium (starch 15 g/L, ferrous sulfate 0.03 g/L, potassium nitrate 1 g/L, dipotassium hydrogen phosphate 0.7 g/L, magnesium sulfate 0.5 g/L, tryptophan 0.5 g/L, adjust pH to 7.0) under a condition of 200 rpm, 25° C. for 36 hours. The Genomic DNA was extracted from *Duganella sp.*B2 CGMCC No 2056 according to the protocol of the genome DNA extraction kit (Shanghai Shenggong).

Figure 1:
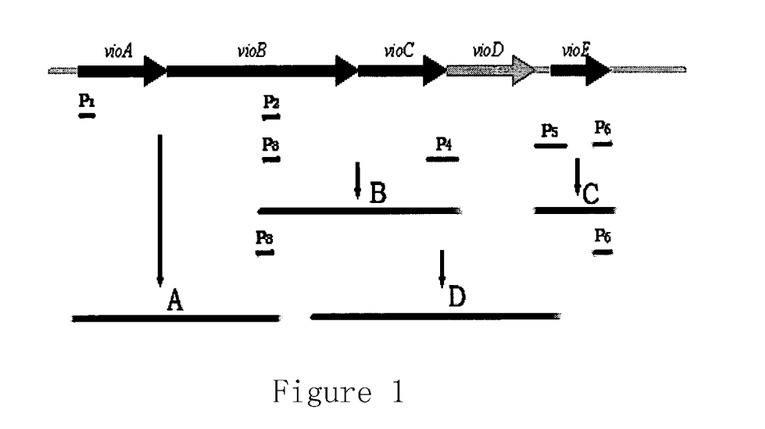
FIG. 1 illustrates the reconstruction of deoxyviolacein biosynthesis related gene cluster by overlap extension PCR.

Three pairs of primers were designed according to the sequence of violacein gene cluster with the software Oligo 7.10. The primer sequences are shown in table 1. Where P1 and P2 were used to amplify vioA and partial gene of vioB, and the amplified products were designated as fragment A; P3 and P4 were used to amplify partial gene of vioB and vioC, and the amplified products were designated as fragment B; P5 and P6 were used to amplify vioE, and the amplified products were designated as fragment C; there are 48 by repeat sequence lies between the two primers P4 and P5 (FIG. 1).

TABLE 1

PCR primers design

| Prime No. | Primers sequence | Restriction enzyme sites |
|---|---|---|
| P1 | 5'-GGATcATTAATGACAAATTATTCTGACATTTGCATAG-3' | Ase I |
| P2 | 5'-AAGAGTGGACTTGGCGGCCGCTTCGACCTG-3' | Not I |
| P3 | 5'-TATAAGCGGCCGCCAAGTCCAC-3' | Not I |

TABLE 1-continued

PCR primers design

| Prime No. | Primers sequence | Restriction enzyme sites |
|---|---|---|
| P4 | 5'-TGGCGTGCGGTGGCATGGCGTCTCCTTAGTTTACCCTTCCAAGTTTGTACC-3' | — |
| P5 | 5'-GGTACAAACTTGGAAGGGTAAACTAAGGAGACGCCATGCCACCGCACG-3' | — |
| P6 | 5'-GGAATGTCCTCGAGTTCCGACACGAAAACGCTGGC-3' | XhoI I |

The primes P1, P2, P3, P4, P5 and P6 and high-fidelity Pfu DNA polymerase were respectively used to amplify with the genome DNA of Duganella as template. PCR reaction system is 50 μL with 0.5 μg DNA template, 25 pmol upper stream and lower stream of the primers, respectively, and 2.5 U Pfu DNA polymerase.

The fragments A and B were amplified using PCR program I listed in table 2, fragment C was amplified using PCR program II listed in table 2.

TABLE 2

PCR amplification program

| PCR program | steps | The numbers of cycling | temperature and time setting |
|---|---|---|---|
| I | 1 | 1 | 94° C., 3 min |
|  | 2 | 30 | 94° C. 1 min, 57° C. 1 min, 72° C. 3 min |
|  | 3 | 1 | 72° C. 10 min |
| II | 1 | 1 | 94° C., 3 min |
|  | 2 | 30 | 94° C. 1 min, 68° C. 1 min, 72° C. 1 min |
|  | 3 | 1 | 72° C. 10 min |
| III | 1 | 1 | 94° C., 3 min |
|  | 2 | 2 | 94° C. 1 min, 50° C. 1 min, 72° C. 5 min |
|  | 3 | 30 | 94° C. 1 min, 50° C. 1 min, 72° C. 5 min |
|  | 4 | 1 | 72° C. 10 min |

PCR product fragments B and C were mixed at volume ratio of 1:1, and after 10 times of dilution the mixture was used as the template for next PCR amplification.

A 50 μL PCR reaction system contained 1.54, mixture of the fragment B and C, and 2.5 U TaKaRa Pfu DNA polymerase. PCR program is the PCR program III. Following the second stage, the program was stopped and 25 μmol of P3 and P6 primers each was added into the reaction system, then the third- and forth-stage of the program were run to produce fragment D by assembling the fragments B and C (FIG. 1). The fragment D was purified according to PCR Purification Kits, and then cloned into pMD18-T vector to obtain pMD18-T-D vector for sequence analysis. The sequencing results showed that the nucleotide sequence of fragment D is the 5'-terminal nucleotide sequence from 3058 to 6198 by of the SEQ ID NO: 1 in the sequence listing.

Figure 2:
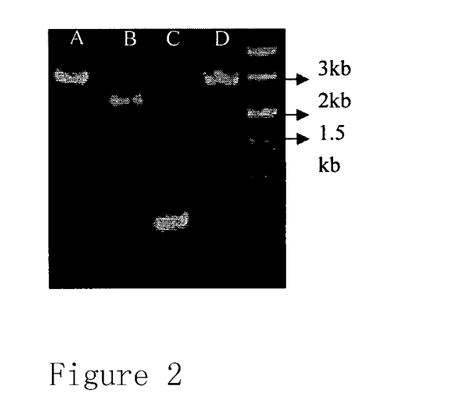
FIG. 2 shows the result of the fragment coding for violacein biosynthesis related gene cluster obtained by PCR amplification.

The results of violacein gene cluster fragment A, B, C and D obtained by PCR amplification were shown in FIG. 2.

The 3057 by fragment A digested with Ase I and Not I, the 3140 by fragment D digested with Xhol I and Not I of pMD18-T-D vector, and the expression vector pET30a digested with Xhol I and Nde I were ligated to construct the recombinant expression vector pET30aVioΔD by using T4 DNA ligase. The recombinant expression vector pET30aVioΔD was transformed into E. coli DH5α, and the transformation product was cultured in LB agar plate containing 100 μg/ml ampicillin. The transformants were selected and cultured to extract the plasmid DNA by alkaline lysis method. A positive clone with insertion fragment was screened and sequenced. Sequencing revealed the nucleotide sequence of fragment VioΔD which is shown in the SEQ ID NO: 1 in the sequence listing. The 5'-terminal nucleotide sequence from 1 to 1308 by of the SEQ ID NO: 1 is VioA which encodes the VioA of violacein biosynthesis pathway; The 5'-terminal nucleotide sequence from 1305 to 4322 by of the SEQ ID NO: 1 is VioB which encodes the VioB of violacein biosynthesis pathway; The 5'-terminal nucleotide sequence from 4323 to 5612 by of the SEQ ID NO: 1 is VioC which encodes the VioC of violacein biosynthesis pathway; The 5'-terminal nucleotide sequence from 5622 to 6197 by of the SEQ ID NO: 1 is VioE which encodes the VioE of violacein biosynthesis pathway. There is no VioD gene of violacein biosynthesis gene cluster in the VioΔD fragment. The Vio ΔD is the deoxyviolacein biosynthesis related gene cluster.

The 3057 by fragment A digested with Ase I and Not I, the 3140 by fragment D digested with Xhol I and Not I of pMD18-T-D vector, and the expression vector pCOM10 (Smits T. H. M. et al., New alkane-responsive expression vectors for E. coli and Pseudomonas. Plasmid 2001. 46, 16-24.) (Tsinghua university) digested with Sal I and Nde I were ligated to construct the recombinant expression vector pCOM10VioΔD by using T4 DNA ligase.

2) Selection of the Expression Host a) The recombinant vector pET30aVioΔD was transformed into E. coli BL21 and E. coli BL21-CodonPlus(DE3)-RIL to obtain the recombinant E. coli BL21-Vio ΔD and E. coli BL21-CodonPlus(DE3)-RIL-VioΔD. The recombinant strains E. coli BL21-pET30a and E. coli BL21-CodonPlus (DE3)-RIL-pET30a obtained by transforming pET30a into E. coli BL21 and E. coli BL21-CodonPlus(DE3)-RIL were used as control.

The recombinant strains were cultured in LB medium at 37° C. and induced at $OD_{600}$ of 0.7 with 0.1 mM IPTG for 30 h at 20° C. Aliquots of 50 mL of fermentation broth were collected and centrifuged at 7000×g for 10 min, and the supernatant was discarded. The cell pellets were then rinsed with 5 mL of ethanol, and mixed by a whirlpool mixer, then shaked for 30 min in a 200 W ultrasonic washing machine, followed by centrifugation at 9000 g for 10 min to recover the ethanol solution.

No blue product was obtained by E. coli BL21-pET30a, E. coli BL21-CodonPlus(DE3)-RIL-pET30a and E. coli BL21-VioΔD; where as blue product was synthesized in E. coli BL21-CodonPlus(DE3)-RIL-VioΔD. This indicated that the four enzymes for deoxyviolacein production from the recombinant expression vector pET30aVioΔD were not expressed correctly or one/some enzyme(s) were expressed in a very low level in *E. coli* BL21, but were expressed correctly in *E. coli* BL21-CodonPlus(DE3)-RIL. Thus, it is possible to speculate that there are rare codes in deoxyviolacein biosynthesis gene cluster. The deoxyviolacein-producing *E. coli* BL21-CodonPlus(DE3)-RIL-VioΔD was named *E. coli* BL-DV.

The atmospheric-vacuum distilled product of the ethanol solution of the blue-purple product obtained from the recombinant strain BL-DV were dissolved in methanol and then analyzed by high-performance liquid chromatography (HPLC, Agilent-1100) with an Agilent Eclipse XDB-C18 column (150 mm×4 mm, 5 μm). The desorption solvent was 70% methanol at a flow rate of 1 mL/min and a temperature of 30° C. The monitoring wavelength was 570 nm.

Figure 3:
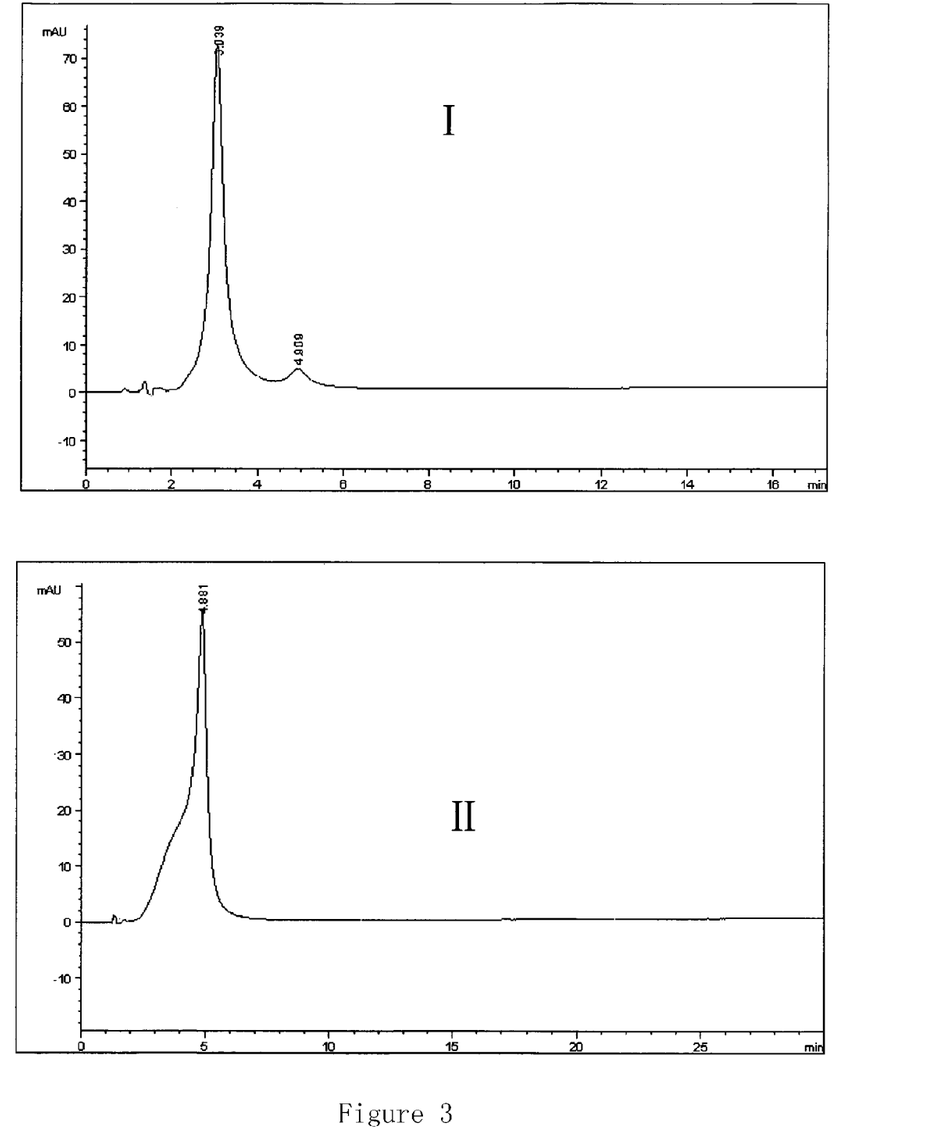
FIG. 3 shows the result of HPLC identification of pigment produced by the recombinant strain *E. coli* BL-DV.

The results of HPLC analysis are shown in FIG. 3. The retention time (4.9 min) of the pigment obtained from the recombinant strain *E. coli* BL-DV CGMCC No. 2557 is consistent with that of deoxyviolacein, the by-product of violacein biosynthesis from *Duganella* B2, with only one HPLC peak. These results indicated that the recombinant vector pET30aVioΔD could express the enzymes for deoxyviolacein biosynthesis correctly and synthesize deoxyviolacien by catalysis in *E. coli* BL21-CodonPlus(DE3)-RIL.

In FIG. 3, I: the HPLC results of the pigment obtained from *Duganella* sp.B2 CGMCC No 2056, where the first peak is violacein and the second peak is deoxyviolacein. II: the HPLC results of crude pigment obtained from the recombinant strain *E. coli* BL-DV.

*E. coli* BL-DV has been deposited in China General Microbiological Culture Collection Center (CGMCC, the Address is: Da Tun Road, Chao Yang District, Beijing, Institute of Microbiology Chinese Academy of Science, post code: 100101) on Jun. 25, 2008, and the accession number of the deposit is CGMCC No. 2557. b) The recombinant vector pCOM10VioΔD was transformed into *Pseudomonas putida* mt-2 NCIMB 10432 to obtain the recombinant *P. putida*-VioΔD. The recombinant strains *P. putida*-pCOM10 obtained by transforming the pCOM10 into *Pseudomonas putida* mt-2 NCIMB 10432 were used as control. The recombinant strains *P. putida*-VioΔD and *P. putida*-p COM10 were cultured in LB medium at 37° C. and induced at $OD_{600}$ of 0.7 with 0.05% (v/v) n-octane for 30 h at 20° C. Aliquots of 50 mL of fermentation broth were collected and then centrifuged at 7000×g for 10 min, the supernatant was discarded. The cell pellets were then rinsed with the same amount of deionized water and mixed by a whirlpool mixer, followed by centrifugation at 7000×g for 10 min to recover the precipitation. The cell pellets were then rinsed with 50 mL ethanol, and completely mixed by a whirlpool mixer, followed by centrifugation at 7000×g for 10 min to transfer the ethanol extract to another clean container. The extraction procedure was repeated until the cells were completely bleached. All the supernatants including crude deoxyviolacein were collected.

No blue product were obtained by the control strain of *P. putida*-pCOM10; whereas the blue product was obtained by *P. putida*-VioΔD.

The atmospheric-vacuum distilled product of the ethanol solution of blue-purple product obtained from the recombinant strain *P. putida*-VioΔD was dissolved in 100% methanol and then analyzed by HPLC (Agilent-1100) with an Agilent Eclipse XDB-C18 column (150 mm×4 mm, 5 μm). The desorption solvent was 70% methanol at a flow rate of 1 mL/min and a temperature of 30° C. The monitoring wavelength was 570 nm.

Figure 4:
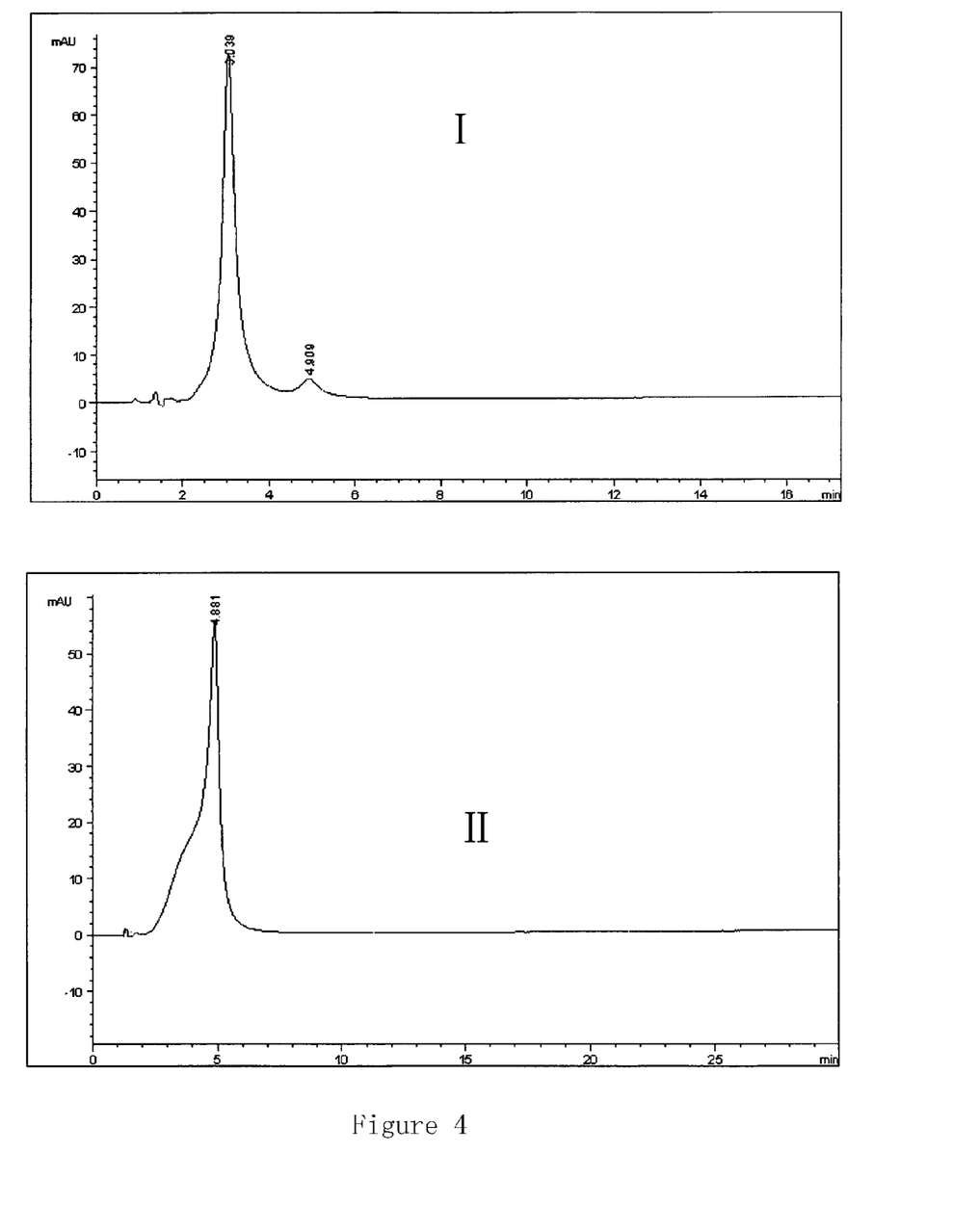
FIG. 4 shows the result of HPLC identification of pigment produced by the recombinant strain *P. putida*-VioΔD.

The results of HPLC analysis are shown in FIG. 4. The retention time (4.9 min) of the blue pigment obtained from the recombinant strain *P. putida*-VioΔD is consistent with that of deoxyviolacein, the by-product of violacein biosynthesis from *Duganella* B2, with only one HPLC peak. These results indicated that the blue product is deoxyviolacein and *P. putida*-VioΔD could correctly express the four enzymes for violacein biosynthesis, VioA, VioB, VioC and VioE, and then synthesize deoxyviolacien.

In FIG. 4, I: the HPLC results of the pigment obtained from *Duganella* sp.B2 CGMCC No 2056, where the first peak is violacein and the second peak is deoxyviolacein. II: the HPLC results of crude pigment obtained from the *P. putida*-VioΔD Embodiment 2: The recombinant strain for producing deoxyviolacein 1) The recombinant strain *E. coli* BL-DV CGMCC No. 2557 for deoxyviolacein production The influence of L-tryptophan, the cell concentration ($OD_{600}$) for inducer (IPTG) addition, the inducer concentration and inducing time on deoxyviolacein production by recombinant strain *E. coli* BL-DV CGMCC No. 2557 were studied by orthogonal experimental design with four factors and three levels. The results are shown in Table 3.

The method for pigment extraction is shown in Embodiment 1. The concentration of the pigment was measured by the maximum absorbance of the pigment sample in ethanol solution. The wavelength for measuring the deoxyviolacien produced by *Duganella* sp B2 was 562 nm with ethanol as blank control. The corresponding pigment concentration was obtained based on the standard curve between absorption value and pigment concentration. Every measurement was repeated 3 times and the results were averaged. The absorption coefficient obtained for the pigment is 9.0955 l·g-1·cm-1.

TABLE 3

The orthogonal experiments design and results

|  | L-trptophan (g/L) | the concentration of inducer (mM/L) | Induce time (h) | $OD_{600}$ | Concentration of Pigment (g/L) |
|---|---|---|---|---|---|
| 1 | 1 (0.2) | 1 (0.7) | 1 (30) | 1 (0.6) | 0.1236 |
| 2 | 1 (0.2) | 2 (1.0) | 2 (35) | 2 (0.8) | 0.1312 |
| 3 | 1 (0.2) | 3 (1.3) | 3 (40) | 3 (1.0) | 0.0145 |
| 4 | 2 (0.4) | 1 (0.7) | 2 (35) | 3 (1.0) | 0.1076 |
| 5 | 2 (0.4) | 2 (1.0) | 3 (40) | 1 (0.6) | 0.1206 |
| 6 | 2 (0.4) | 3 (1.3) | 1 (30) | 2 (0.8) | 0.1542 |
| 7 | 3 (0.6) | 1 (0.7) | 3 (40) | 2 (0.8) | 0.1261 |
| 8 | 3 (0.6) | 2 (1.0) | 1 (30) | 3 (1.0) | 0.0815 |
| 9 | 3 (0.6) | 3 (1.3) | 2 (35) | 1 (0.6) | 0.1244 |
| average 1 | 0.090 | 0.119 | 0.120 | 0.123 |  |
| average 2 | 0.127 | 0.111 | 0.121 | 0.137 |  |
| average 3 | 0.111 | 0.098 | 0.087 | 0.068 |  |
| range | 0.037 | 0.021 | 0.034 | 0.069 |  |

The results in Table 3 showed that the significance for influencing deoxyviolacein production was in the order of cell concentration>L-trptophan>induce time>inducer concentration. And the optimum combination was determined as: 0.4 g/L L-tryptophan supplement in LB medium, 1.0 mmol/L inducer (IPTG), and cell concentration of $OD_{600}$=0.8 for the IPTG induction.

At the optimum conditions, three verification tests have been done and the deoxyviolacein production was obtained as 0.183 g/L, 0.165 g/L and 0.153 g/L respectively, with the average of 0.167 g/L.

2) The Recombinant Strain *P. putida*-VioΔD for producing deoxyviolacein

*P. putida*-VioΔD was inoculated into E2 liquid medium ($NaH_2PO_4 \cdot 2H_2O$ 1.3 g/L, $Na_2HPO_4 \cdot 12H_2O$ 3.0 g/L, $NH_4Cl$ 0.9 g/L, K$_2$HPO$_4$.3H$_2$O 7.5 g/L, 100 mM MgSO$_4$.7H$_2$O 10 mL/L, glycerol 3 mL/L, yeast extract 1.0 g/L, adjust pH to 7.0) containing 0.4 g/L L-tryptophan under 200 rpm, 30° C. overnight. Then the culture medium (overnight) was inoculated into fresh E2 liquid medium containing 0.4 g/L L-tryptophan and 50 μg/ml kanamycin with 10% inoculums, and cultured at 30° C. for 3-4 h, and the inducer n-octane was added into the fermentation broth when the OD$_{600}$ reached 1.0. The cultivation temperature was then shifted to 20° C. for 30 h, followed by centrifugation to recover the cells. The recovered cells were completely mixed with ethanol, and the ethanol extract of blue-violet pigment was separated from the cells by centrifugation.

*Duganella sp.*B2 CGMCC No 2056 was inoculated into liquid medium (starch 15 g/L, ferrous sulfate 0.03 g/L, potassium nitrate 1 g/L, dipotassium hydrogen phosphate 0.7 g/L, magnesium sulfate 0.5 g/L, tryptophan 0.5 g/L, adjust pH to 7.0) under 200 rpm, 25° C. for 36 hours, followed by centrifugation to recover the cells. The recovered cells were completely mixed with ethanol, and the ethanol extraction of the blue-violet pigment was separated from the cells by centrifugation.

The two blue-purple products were analyzed by HPLC, and the method is shown in Embodiment 1.

The HPLC results for the blue-violet product from *P. putida*-VioΔD showed that the blue-violet product is deoxyviolacein. The HPLC results for the blue-violet product from *Duganella sp.*B2 CGMCC No 2056 showed that the blue-violet product is a mixture of violacein and deoxyviolacein.

The quantitative analysis for deoxyviolacein produced by *P. putida*-VioΔD and *Duganella* sp.B2 CGMCC No 2056 was conducted, respectively.

The quantitative analysis was conducted by measuring the absorbance of the ethanol solution of the blue-violet pigment at the maximum absorption. The wavelength for measuring deoxyviolacien produced by *Duganella* sp B2 was 562 nm with ethanolal as blank control. The corresponding pigment concentration was obtained based on the standard curve between absorption value and pigment concentration. Every measurement was repeated 3 times and the results were averaged. The absorption coefficient obtained is 14.852 l·g-1·cm-1.

The quantitative analysis results showed that the deoxyviolacein production of *P. putida*-Viol D was the highest and the final production was 1.5 g/L (average), which is much higher than the deoxyviolacein produced by *Duganella* sp.B2 CGMCC No 2056 (0.16 g/L).

Industrial Application

Deoxyviolacein is a by-product of violacein biosynthesis in many wild strains with low productivity and difficulty in separation, resulting in the entire restriction of its scientific research, large-scale production and application. The *E. coli* BL-DV CGMCC No. 2557 and *P. putida*-VioΔD could produce deoxyvilacein with high yields. The deoxyviolacein production by *E. coli* BL-DV CGMCC No. 2557 reached 0.17 g/L fermentation broth, and the deoxyviolacein production by *P. putida*-VioΔD reached 1.5 g/L fermentation broth through Erlenmeyer flask liquid fermentation. Moreover, the deoxyviolacein produced is convenient to extract, and easy to separate and purify. The recombinant strains are *E. coli* or *P. putida*, which can be easily controlled and industrialized for production of deoxyviolacein.

The invention claimed is:

1. An isolated deoxyviolacein synthesis-related gene cluster comprising
a polynucleotide comprising SEQ ID NO: 1.

2. A recombinant *E. coli* for producing deoxyviolacein which comprises
a deoxyviolacein synthesis-related isolated gene cluster comprising
a polynucleotide comprising SEQ ID NO: 1,
wherein
the recombinant *E. coli* is obtained by introducing the isolated gene cluster into *E. coli* B L21-CodonPlus (DE3)-RIL .

3. The recombinant *E. coli* according to claim 2, wherein said recombinant *E. coli* is *E .coli* BL-DV CGMCC No.2557.

4. A recombinant *P. putida* for producing deoxyviolacein which comprises
an isolated deoxyviolacein synthesis-related gene cluster comprising
a polynucleotide comprising SEQ ID NO: 1,
wherein the recombinant *P. putida* is obtained by introducing the isolated gene cluster into *P. putida* mt-2.

5. The recombinant *P. putida* according to claim 4, wherein said recombinant *P. putida* is *P. putida* mt-2 NCIMB 10432 (VioABCE).

6. An expression cassette comprising an isolated deoxyviolacein synthesis-related gene cluster comprising a polynucleotide comprising SEQ ID NO: 1.

7. A recombinant expression vector comprising
an expression cassette having an isolated deoxyviolacein synthesis-related gene cluster comprising
a polynucleotide comprising SEQ ID NO: 1.

* * * * *